United States Patent
Story et al.

(10) Patent No.: US 8,323,642 B2
(45) Date of Patent: Dec. 4, 2012

(54) TISSUE FUSION METHOD USING COLLAGENASE FOR REPAIR OF SOFT TISSUE

(75) Inventors: Brooks J. Story, Franklin, MA (US); Ed Yiling Lu, Chestnut Hill, MA (US); Donna Torres, Atileboro, MA (US)

(73) Assignee: DePuy Mitek, Inc., Raynham, MA (US)

(*) Notice: Subject to any disclaimer, the term of this patent is extended or adjusted under 35 U.S.C. 154(b) by 298 days.

(21) Appl. No.: 11/637,983

(22) Filed: Dec. 13, 2006

(65) Prior Publication Data
US 2008/0145357 A1 Jun. 19, 2008

(51) Int. Cl.
*A61K 38/46* (2006.01)
(52) U.S. Cl. .................. 424/94.67; 623/14.12
(58) Field of Classification Search .............. 424/94.67; 623/14.12
See application file for complete search history.

(56) References Cited

U.S. PATENT DOCUMENTS

| | | | |
|---|---|---|---|
| 3,201,324 A | 8/1965 | Barton et al. | |
| 3,201,325 A | 8/1965 | Barton | |
| 3,678,158 A | 7/1972 | Sussman | |
| 3,705,083 A | 12/1972 | Chiuli et al. | |
| 3,821,364 A | 6/1974 | Chiuli et al. | |
| 4,174,389 A | 11/1979 | Cope | |
| 4,338,300 A | 7/1982 | Gelbard | |
| 4,524,065 A * | 6/1985 | Pinnell | 424/94.2 |
| 5,132,119 A | 7/1992 | Lee | |
| 5,252,481 A | 10/1993 | Holjevac et al. | |
| 5,332,503 A | 7/1994 | Lee et al. | |
| 5,500,000 A * | 3/1996 | Feagin et al. | 606/232 |
| 5,514,370 A | 5/1996 | Stern et al. | |
| 5,753,485 A | 5/1998 | Dwulet et al. | |
| 5,830,741 A | 11/1998 | Dwulet et al. | |
| 5,842,477 A | 12/1998 | Naughton et al. | |
| 5,902,609 A | 5/1999 | Lee | |
| 5,989,888 A | 11/1999 | Dwulet et al. | |
| 6,022,539 A | 2/2000 | Wegman | |
| 6,146,626 A | 11/2000 | Markert et al. | |
| 6,353,028 B2 | 3/2002 | Easterling | |
| 6,379,667 B1 | 4/2002 | Khaw et al. | |
| 6,455,569 B1 | 9/2002 | Ferguson | |
| 6,475,764 B1 | 11/2002 | Burtscher et al. | |
| 6,638,949 B1 | 10/2003 | Folkman et al. | |
| 6,759,432 B2 | 7/2004 | Khaw et al. | |
| 2001/0006630 A1 | 7/2001 | Yacoby-Zeevi | |
| 2001/0020476 A1 | 9/2001 | Gan et al. | |
| 2002/0164319 A1 | 11/2002 | Khaw et al. | |
| 2003/0022856 A1 | 1/2003 | Richardson et al. | |
| 2003/0147876 A1 | 8/2003 | Ni et al. | |
| 2004/0010306 A1 | 1/2004 | Freyman et al. | |
| 2004/0175371 A1 | 9/2004 | Yacoby-Zeevi | |
| 2004/0202702 A1 | 10/2004 | Studin | |
| 2004/0265294 A1 | 12/2004 | Franano | |
| 2005/0079159 A1 | 4/2005 | Shastri et al. | |
| 2005/0234549 A1 * | 10/2005 | Kladakis et al. | 623/14.12 |
| 2006/0247790 A1 * | 11/2006 | McKay | 623/23.44 |

FOREIGN PATENT DOCUMENTS

| | | |
|---|---|---|
| EP | 0479615 A1 | 4/1992 |
| EP | 0677586 A1 | 10/1995 |
| JP | 2004357694 A | 12/2004 |
| WO | WO 2006078870 A2 | 7/2006 |

OTHER PUBLICATIONS

Porat et al. 1985. Increased Collagenolytic Activity in Severed and Sutured Tendons Following Topical Application of Exogenous Collagen in Chickens. Journal of Orthopaedic Research. 3:43-48.*
Riley et al. 2005. Collagenase Promotes the Cellular Responses to Injury and Wound Healing In Vivo. Journal of Burns and Wounds. vol. 4:112-124.*
Full Thickness Wounds. 2010. Tyco Healthcare. http://www.dhphomedelivery.com/wound-care-full-thickness.pdf. p. 1-8.*
Bos et al. Specific Enzymatic Treatment of Bovine and Human Articular Cartilage. Arthritis & Rheumatism vol. 46, No. 4, Apr. 2002, pp. 976-985.*
Collagenase from Clostridium histolyticum. Sigma-Aldrich 2012 downloaded from http://www.sigmaaldrich.com/catalog/product/sigma/c2799?lang=en&region=US. p. 1-3.*
Information on EC 3.4.24.3—microbial collagenase. downloaded on Mar. 12, 2012 from http://www.brenda-enzymes.org/php/flat_result.php4?ecno=3.4.24.3&organism_list=&Suc. p. 1-2 only.*
Information on EC 3.4.24.7—interstitial collagenase. downloaded on Mar. 13, 2012 from http://www.brenda-enzymes.org/php/flat_result.php4?ecno=3.4.24.7&organism_list=&Suc. p. 1-3 only.*
European Search Report Application No. 07254840.7, dated Sep. 11, 2011.
Cao, Y. et al., Bridging Tendon Defects Using Autologous Tenocyte Engineered Tendon in a Hen Model, Plastic and Reconstructive Surgery, Oct. 1, 2002, pp. 1280-1289, vol. 110, No. 5, Williams and Wilkins Co., Baltimore, MD.

* cited by examiner

*Primary Examiner* — Taeyoon Kim

(57) ABSTRACT

The present invention provides a method of using locally administered collagenase as a non-invasive means of enhancing cell release from the cartilage or fibrocartilage tissues adjacent to a disease or injury site. The subsequent migration of cells from these tissues into the lesion or wound, followed by deposition of the appropriate extracellular matrix, results in closure of the lesion or fusion of a tissue gap.

16 Claims, No Drawings

TISSUE FUSION METHOD USING COLLAGENASE FOR REPAIR OF SOFT TISSUE

FIELD OF THE INVENTION

The field of art to which this invention relates is compositions for use in methods of treating and repairing soft tissue, more particularly collagenase compositions and methods of using such compositions for tissue fusion to treat or repair soft tissue.

BACKGROUND OF THE INVENTION

Tissue healing is a complex process involving cells, matrix components and biological factors. Whether the damage to the tissue is caused by injury or disease, a key component of tissue healing is the migration of native cells from surrounding tissue into the wound or lesion, where they can participate in the healing process, whether by interaction with each other, expression of the appropriate biological factors or by the deposition of new extracellular matrix (ECM). In most tissues, this is accomplished by immediate massive matrix degradation via a post-injury response. In the case of vascularized tissue, matrix metalloproteinases (MMPs), e.g., collagenases, are released into the area by infiltrating cells of neutrophils and macrophages. These agents remove degraded tissue, and also break down the ECM in the periphery of the adjacent healthy tissues. This allows the necessary cell migration into the repair site. Thus, the removal of unwanted tissue is directly connected to matrix degradation in the wound area. In avascular tissues such as articular cartilage and the so-called "white zone" of the meniscus, migration of native chondrocytes or fibrochondrocytes from surrounding tissues into the healing site is negligible due to the lack of infiltrating cells through blood vessels, the rigidity of the collagenous matrix which surrounds them, and the relatively low concentration of native collagenases. Consequently, such tissues often do not heal to any significant degree after an acute injury or long term tissue degeneration. In the case of cartilage lesions, because of the inefficient matrix degradation, fibrous tissue sometimes fills the defect gap. However, such fibrous tissue is not mechanically suitable as a replacement for the native tissue.

Transplantation of autologous cartilage tissue has been developed to repair large articular cartilage lesions. Current methods typically involve harvesting a plug(s) of osteochondral tissue from a healthy, non-loaded cartilage surface, followed by transplantation into the defect site. While the transplanted tissue often integrates with the native subchondral bone, the method often suffers from poor integration at the peripheral interface between native and transplanted cartilage.

A technique known as microfracture has been used to encourage ingrowth of fibrocartilage tissue in small articular defects. This procedure involves drilling small holes into the underlying subchondral bone, the effect of which is alleged to be the release of marrow stem cells and healing agents into the defect site. The result is the formation of tissue which is generally fibrous. Although this method does produce the effect of tissue filling, the new tissue is not true cartilage and therefore cannot withstand long term articular loading. To address this shortcoming, so-called autologous chondrocyte implantation (ACI) methods have been developed. However, the long-term clinical benefit of the method still needs to be established.

To overcome the problem of cartilage integration there have been attempts to use laser-based thermal welding procedure to promote tissue fusion in intervertebral disc, cartilage and meniscus repairs. The primary shortcoming of this technology is that the procedure produces substantial heat, often resulting in death of local cells that are the vital source for rebuilding the tissue. A suitable balance between thermally driven tissue welding and cell viability is apparently difficult to achieve.

In the case of white zone meniscus injury, the edges of a tear seldom fuse even when held tightly together with anchors or suture. Surgical resection is currently the standard of care for such injuries, which often results in long-term degeneration of the underlying articular cartilage. Similar difficulties are encountered in the repair of the so-called triangular fibrocartilage complex (TFCC), a meniscus-like structure at the base of the wrist, as well as in the repair of ligament, tendon and intervertebral disc injuries.

Accordingly, it can be seen that there is a need in this art for improved methods of treating and repairing defects and injuries in cartilage and other soft tissues.

SUMMARY OF THE INVENTION

A novel method of fusing tissue for treating defects and injuries in meniscal and articular cartilage and other soft tissue is disclosed. In the method of the present invention, a therapeutically effective amount of a collagenase composition is applied to soft tissue at the site of a defect or injury. Collagenases are enzymes that degrade collagens, ECM specific abundant proteins, and are not generally detrimental to cells.

In the method of the present invention, collagenase is applied transiently to digest collagen at the surfaces of the defect or injury, thereby mobilizing chondrocytes or fibrochondrocytes. It is believed that the cells can then migrate into the defect or injury site, where they can proliferate and deposit new extracellular matrix, thereby fusing the tissue. This resultant healing of the avascular tissues, as opposed to a vascular healing mechanism, is herein termed tissue fusion. The procedure may be performed in either intracorporeal or extracorporeal fashion. In an extracorporeal procedure, the damaged soft tissue is removed from the patient, treated with the collagenase composition and then re-implanted into the patient.

The novel method of the present invention has many advantages. The present invention can be used to provide a bonding mechanism between transplant and native cartilage in the repair of non self-healing defects. It can also be used to promote healing of injuries to other cartilaginous tissue such as avascular regions of the meniscus. In addition, cell death is not an issue for the proposed collagenase treatment for promoting tissue fusion. Collagenases are natural and ubiquitously expressed enzymes which only target extracellular matrix collagens, not the cell body itself. As such, cells of various kinds are very tolerant to collagenases, unlike broad-spectrum proteases such as trypsin which are known to be cytotoxic. The use of the method of the present invention promotes and accelerates the natural healing process, and improves the outcome of tissue repair surgical procedures. The method of the present invention may be used to fuse tissue in a variety of conventional surgical procedures, including osteochondral implantation or transplantation, repair of white zone meniscal injuries, repairs of TFCC injuries, etc.

These and other advantages and aspects of the present invention will become more apparent from the following description and accompanying drawings.

DETAILED DESCRIPTION OF THE INVENTION

As mentioned above, the term "tissue fusion" as used herein is defined to mean the healing of avascular tissues. There are numerous soft tissue repair procedures in which the novel tissue fusion method of the present invention may be utilized.

The present invention can be used to improve the effectiveness of osteochondral transplantation or implantation procedures. Use of the collagenase in the method of the present invention can be used to enhance the bonding and provide tissue fusion between transplant and native cartilage in the repair of cartilage defects.

Unlike thermal welding techniques, cell death is not an issue for the collagenase treatment of the present invention for promoting tissue fusion. Collagenases are natural and ubiquitously expressed enzymes which only target extracellular matrix collagens, not the cell body itself. Cells of various kinds are very tolerant to collagenases, unlike broad spectrum proteases such as trypsin which are known to be cytotoxic.

For white zone meniscal tears, a collagenase composition is applied to the faces of the damaged tissue to provide local digestion of the matrix and thus to release embedded cells in addition to the suturing, overcoming the limitations of mechanical fixation and providing for tissue fusion and improved healing. The local digestion provided by the method of the present invention can also be used in conjunction with an adhesive to repair a tear in the white zone of the meniscus. The collagenase is combined with or used prior to the application of an adhesive that will provide sufficiently effective apposition and fixation of the tear surfaces while allowing for the enzyme to digest the matrix. The collagenases can also be applied to the tissue first and the adhesive is then applied in a layer over the reapproximated tear to provide fixation and possibly act to seal in the enzyme while preventing synovial fluid from entering the tear. The fixation of the tear can also be done using an adjunct conventional meniscal repair device, and the delivery of the collagenases to the tear surfaces can either be done using a conventional application technique such as a syringe, microsyringe array, needle-free injection system, or could be accomplished via the repair device itself. If desired, and if the practitioner were willing to accept any attendant disadvantages, the white zone tear may be repaired by the direct application of the collagenase compositions of the present invention without the use of any ancillary mechanical fixation or adhesives.

In the practice of the present invention, it is particularly preferred to use one or more collagenases produced by the bacterium *clostridium histolyticum*. Several authors have reported at least two distinct collagenases produced by fermentation of *c. histolyticum*. It has been reported that the purified, individual collagenases have different activities on native collagen. In so-called crude collagenase preparations, additional components may include trypsin, caseinase and clostripain. These components may affect the specificity of the collagenase preparation. The collagenases used for this invention may also be mammalian or recombinant in nature. The collagenases that can be used in the practice of the present invention include collagenase 1 (MMP-1), collagenase 2 (MMP-8), collagenase 3 (MMP-13).

A therapeutically effective amount of the collagenases will be used in the practice of the present invention. The amount will be sufficient to effectively provide tissue fusion. For example, in in vitro repair, the concentration may be between 266 U/ml and 273 U/ml, when treated for 10 minutes at room temperature. Concentrations will vary depending upon duration and temperature and depending upon whether the administration is in vivo or in vitro.

The carriers that can be used for the collagenases in the practice of the present invention include conventionally used carriers for pharmaceutical products and may include gels or liquids comprising hyaluronic acid, chondroitin sulfate, saline, platelet rich plasma, or fibrin glue. Various types of biodegradable surgical meshes, woven fabrics, felts, or non-woven fabrics may also be used as a carrier for the collagenase composition. Such a mesh would be resorbed as newly deposited tissue infiltrated the mesh, thereby creating volume for still more ECM deposition. Examples of polymers and co-polymers that can be used in the carrier of the present invention include homopolymers, such as poly(glycolide), poly(lactide), poly(epsilon-caprolactone), poly(trimethylene carbonate) and poly(para-dioxanone); copolymers, such as poly(lactide-co-glycolide), poly(epsilon-caprolactone-co-glycolide), and poly(glycolide-co-trimethylene carbonate). The polymers may be statistically random copolymers, segmented copolymers, block copolymers or graft copolymers. Other polymers include albumin; casein; waxes such as fatty acid esters of glycerol, glycerol monostearate and glycerol distearate; starch, crosslinked starch; simple sugars such as glucose, ficoll, and polysucrose; polyvinyl alcohol; gelatine; modified celluloses such as carboxymethylcellulose (CMC), hydroxymethyl cellulose, hydroxyethyl cellulose (HEC), hydroxypropyl cellulose, hydroxypropyl-ethyl cellulose, hydroxypropyl-methyl cellulose (HPMC), sodium carboxymethyl cellulose, oxidized regenerated cellulose, and cellulose acetate; sodium alginate; hyaluronic acid and derivatives; polyvinyl pyrollidone; polymaleic anhydride esters; polyortho esters; polyethyleneimine; glycols such as polyethylene glycol, methoxypolyethylene glycol, and ethoxypolyethylene glycol, polyethylene oxide; poly(1,3 bis (p-carboxyphenoxy) propane-co-sebacic anhydride; N,N-diethylaminoacetate; and block copolymers of polyoxyethylene and polyoxypropylene and combinations thereof. For example, the carrier may comprise any substance that is suitable for the local delivery of growth factors, proteins, pharmaceuticals, or other large molecules.

It is also be possible to deliver the collagenase composition via biocompatible, nonresorbable carriers. In this embodiment, the carrier would provide a permanent matrix for the infiltration of cells released by the collagenase composition and for the deposition of new ECM. The nonresorbable mesh might also provide permanent reinforcement for the repaired tissue. Materials for such a nonresorbable carrier may include polypropylene, polyethylene, polytetrafluoroethylene (PTFE), and polyester.

The collagenase carrier can also be formulated to be semi-resorbable, that is, part of the carrier would be resorbable and the other part would be nonresorbable. Components for such a mesh could be selected from the lists of materials included herein. Such a carrier would combine the advantages of resorbable and nonresorbable carriers by allowing progressively larger volume for infiltration of new tissue in addition to permanent mechanical reinforcement of the repair site.

The collagenases in the various dosage forms will be sterile, and various conventionally known sterilization and/or aseptic techniques can be used to obtain the requisite sterility. The selection of the appropriate dosage form will depend upon the type of procedure and the type of tissue and the nature of the defect or injury.

The collagenase compositions of the present invention may also contain conventional biocompatible adhesives such as fibrin glues (autologous or allogenic), cyanoacrylates, isocyanates, polyurethanes, and the like and equivalents thereof.

It is desirable to confine the collagenases to the vicinity of the soft tissue injury repair site to minimize coincidental collagen digestion in adjacent tissues. However, total containment to the repair site may not be possible. Another embodiment of the present invention is to provide a sufficiently effective amount of a collagenase scavenger to the region surrounding the collagenase application site. The scavenger is preferably a collagen solution, the collagen molecules of which would be attacked by any collagenase that escaped the repair site, thereby neutralizing the escaped collagenase. The scavenger solution may comprise allogenic, xenogenic or autologous collagen that has been extracted from collagenous tissues.

The present invention is believed to be particularly effective for the treatment of cartilage fissures and small cartilage lesions, not larger than about one centimeter in width, although larger fissures and lesions may be effectively treated. In such cases, the periphery of the lesion comprising healthy cartilage tissue will be exposed to one or more collagenases. This may be accomplished by a variety of methods, for example, direct injection of the edges of the defect with an aqueous collagenase solution, or fixation of an intra-defect, collagenase-loaded implant. To aid in the establishment of repair tissue, the patient may be immobilized or placed in restricted motion.

Enhancement of Tissue Integration of Osteochondral Autografts

In certain instances, a conventional osteochondral autograft procedure may have limitations in the size of defect which can be treated. At a certain limit, the number of released cells may not be able to generate sufficient extracellular matrix to fill the defect. However, the collagenase method will be an effective complement to techniques for osteochondral autograft, such as osteochondral transplantation and Mosaicplasty. The long-term success of these techniques depends not only on the chondrocyte viability but also on peripheral integration of the implant with surrounding tissue. The present invention facilitates lateral migration of chondrocytes and subsequent integration of native and transplanted tissue. The technique involves injection into or coating of the lateral surface of the native tissue adjacent to the transplanted plug. Released chondrocytes then infiltrate the tissue/transplant interface and produce the appropriate cartilaginous extracellular matrix, thereby fusing the tissue and transplant surfaces. Optionally, the donor plug can be partially or totally immersed in a collagenase solution prior to placement in the defect.

In a further embodiment for articular cartilage repair, a synthetic material can be used to fill the cartilage defect, such as the commercially available TruFit osteochondral plug, manufactured by OsteoBiologics Inc. The TruFit osteochondral plug comprises a porous composite of biodegradable materials, including polylactide-co-glycolide (PLGA), calcium sulfate and PGA fibers. Such devices are substantially porous to allow the ingrowth of articular cartilage into the implant. A collagenase composition is infused into and/or on the cartilage contacting section of the plug. Following implantation, release of the collagenase acts to digest the periphery of the cartilage defect, thereby releasing cells and enhancing their ability to infiltrate the porous implant and deposit new cartilage tissue.

In either transplantation or implantation procedures for cartilage defect repair, the objective is to effect collagenase release into the cartilage that is peripheral to the implant. However, release of collagenase from the top surface of the implant may be undesirable in certain cases due to coincident partial digestion of surrounding collagenous tissue. As such, it may be necessary to employ a barrier on the top surface of the implant. For example, if a cylindrical plug were used, the surface barrier would allow radial collagenase release into the periphery of the cartilage defect, but would prevent axial release of collagenase into the knee joint.

Repair of White Zone Meniscal Tears

In a preferred embodiment, white zone meniscal tears are treated by exposing each face of the tissue gap to collagenase. The faces of the tear are then be brought together by use of conventional mechanical fixation procedures, for example, conventional sutures, screws, barbed members, tacks, and the like. Through fibrochondrocyte release and ECM production as described above, the faces of the torn meniscus are fused by newly created native tissue.

Another embodiment of white zone meniscal repair involves interposition of a thin, porous, collagenase-impregnated fabric or other scaffold. Upon mechanical interposition between the faces of the tear, this device releases collagenase into the damaged tissue, and then serves as a scaffold for the released fibrochondrocytes and the subsequently produced extracellular matrix. Preferably, a conventional method of mechanically closing the tear is also utilized, for example employing sutures, implantable meniscal repair devices, or device/suture hybrid meniscal repair devices to mechanically close the tear. This method ensures that the faces of the tear are in close proximity to each other, and preferably in intimate contact with each other, thereby minimizing the cell migration distance required to effect deposition of new ECM. There are a number of known, commercially available devices for meniscal repair that may be suitable for the mechanical fixation, and the selection of a particular fixation device is within the discretion and preference of the surgeon.

Repair of TFCC Tears

Similar to white zone meniscal tears in the knee, many injuries of the triangular fibrocartilage complex (TFCC) of the wrist do not heal naturally. These injuries are treated in an analogous manner to meniscal tears, using collagenase treatment of the wound surfaces, followed by mechanical fixation and healing via the production of new native tissue.

Enhanced Repair Using Autologous Chondrocyte Implantation ("ACI")

In addition to the osteochondral transplantation and implantation procedures described above, collagenase compositions of the present invention can be used to enhance the effectiveness of so-called autologous chondrocyte implantation (ACI). By including a collagenase composition with the autologous chondrocytes, the periphery of the cartilage defect could be partially digested, thereby enhancing peripheral integration of the ACI implant with the surrounding native tissue, in a similar fashion to the method described for osteochondral implantation or transplantation.

Repair of Tendons and Ligaments

It is known that some tendons and ligaments are relatively avascular. For example, the anterior cruciate ligament (ACL) is not highly vascularized and as such has limited capacity for healing, especially in older patients. Similarly the tendons of the rotator cuff are often highly avascular in older patients, and repair of these tendons is known to suffer from high failure fates. This is due to the low healing capacity of the repaired tendon. The collagenase compositions of the present invention can be used in a tendon or ligament repair procedure to mobilize tenocytes so that they could participate in the healing process. For example, a flexor tendon repair procedure would be conducted in the following manner: A collagenase composition is applied to the ends of a lacerated tendon. The ends of the tendon are re-approximated using a conventionally known core suture technique, followed by epitendinous suturing around the periphery of the repair.

Extracorporeal Repair Procedure

Collagenase compositions may also be employed in an extracorporeal procedure. For example, the patient's meniscus is surgically removed, either partially or entirely, followed by treatment of the meniscal tear surfaces with collagenase, using the methods described herein. Following collagenase treatment, the meniscus is reimplanted. The advantage of this approach is that the accuracy of collagenase delivery may be improved by having full, unobstructed access to the meniscal injury site as might be encountered in an arthroscopic procedure. Also, in using this technique the tissue can be thoroughly rinsed to remove all residual collagenase prior to reimplantation, thereby minimizing the exposure of other tissues to collagenase.

By applying the principles outlined above, additional applications of the method of the present invention using collagenase are envisioned. Such applications include, but are not limited to the following: The method may be used to provide tissue bonding for fissure defects in intervertebral disc (IVD) repair. The method of the present invention may also be used to provide tissue bonding for the repair of fibrocartilaginous structures such as ligaments and tendons.

The method of the present invention utilizing collagenases to provide tissue fusion has many advantages. It provides a unique and biological tissue integration enhancing strategy. It also provides a method for treating injured or diseased cartilage and fibrocartilage tissues; it is known that such cartilage and tissues have a limited capacity for natural healing. The method fuses tears and gaps in avascular tissue such as white zone meniscus and TFCC. It also eliminates the need for the surgical removal of injured or diseased tissues such as a torn meniscus. Utilizing the method of the present invention to preserve meniscus prolongs the life of underlying knee cartilage. The present invention provides a method that can be implemented arthroscopically. The present method may improve the outcome of autologous chondrocyte implantation techniques through fusion of the tissue/implant interface.

The following examples are illustrative of the principles and practice of the present invention, although not limited thereto.

EXAMPLE 1

The meniscus of the knee has a dense fibrous collagen structure, relatively few cells, and a very limited capacity for spontaneous healing. Healing is especially difficult in the avascular (white-white) portions of the meniscus. The following experiment was conducted to test meniscal tissue repair using collagenase application, both alone and in combination with a cyanoacrylate adhesive and a fibrin sealant. The cyanoacrylate adhesive was selected because it is a strong adhesive that could provide stable physical approximation of the surfaces to be repaired while the collagenase allowed for cellular migration into the tear. The fibrin glue sealant was also tested as it is a biocompatible adhesive, although with less adhesive strength than cyanoacrylate.

Materials and Methods

Bovine calf knees were obtained fresh and the menisci removed under sterile conditions. The menisci were stored overnight at 4° C. in a solution of DMEM and gentamicin prior to treatment with collagenase and incubation. An 8-mm biopsy punch was used to punch four samples from each meniscus. The samples were then trimmed to a 2-mm thickness, and a 3-mm biopsy punch was used to core a section from the center of the 8-mm disk. Collagenase solutions were prepared by reconstituting lyophilized collagenase (Worthington Biochemical, Type 2, CLSS-2, 273 U/mg) in D-PBS with calcium chloride. The samples were submerged in the collagenase solution (1 mg/ml) for 10 minutes and then rinsed thoroughly in PBS. Test articles receiving collagenase treatment only were reassembled and incubated at 37° C., 5% $CO_2$ for 6 weeks. Samples that were to be treated with cyanoacrylate adhesive (Dermabond Topical Skin Adhesive, 2-Octyl Cyanoacrylate, High Viscosity, Ethicon, Catalog #DPP6) alone or in combination with collagenase were reassembled and a drop of the adhesive was placed on the top surface of the 8-mm disk and spread out to form a thin layer completely covering the surface. A drop of the fibrin sealant (Crosseal Fibrin Sealant (human), Ethicon) was applied to the center section of the cored samples following collagenase treatment (if applicable) prior to the center core being replaced.

After 6 weeks the test articles were fixed in formalin and processed for paraffin embedding. Paraffin sections were stained with H&E and examined using light microscopy. Grades from 0 (no healing) to 3 (complete healing) were used to score the healing seen in the sections.

Results

Histology of the collagenase-treated test articles revealed that several of the samples in that group appeared to have healed completely. The average histology scores for the five test groups and the untreated controls are contained in Table 1. Most collagenase treated test articles were graded as either 2 or 3.

TABLE 1

| Treatment Group | Mean Histology Score (± s.d.) |
| --- | --- |
| Untreated Control | 1.8 ± 1.3 |
| Collagenase | 2.4 ± 0.7 |
| Dermabond | 1.0 ± 0.0 |
| Collagenase + Dermabond | 1.3 ± 1.2 |
| Fibrin | 1.0 ± 1.4 |
| Collagenase + Fibrin | 1.3 ± 0.6 |

Several collagenase treated test articles appear to have repaired completely (Grade 3). The tear surfaces that had been created are no longer distinguishable from the rest of the tissue.

All Dermabond-treated test articles had some apparent healing at the surface away from the one to which the Dermabond was applied. At the Dermabond treated surface, test articles typically were not healed.

Test articles treated with the fibrin glue alone varied in the degree of healing seen. In one test article the healing of the tissue appeared to be complete while in others there was no apparent repair of the tissue.

Healing in untreated control test articles also varied, with one showing complete healing, two showing partial healing, and one other showing no healing.

The healing in the tissue that was treated with both collagenase and Dermabond also varied. Two of the test articles had partial repair, while a third showed no healing at all Test articles treated with collagenase and fibrin glue scored either 1 or 2 for repair.

EXAMPLE 2

Repair of Meniscal Tissue Following Collagenase Treatment: Summary of In Vitro Testing Using a Chronic Tear Model The studies conducted in Example 1 showed that collagenase treatment of acute tears in bovine calf meniscal tissue resulted in improved repair of the tissue in vitro. The meniscus of the knee has a dense fibrous collagen structure, relatively few cells, and a very limited capacity for healing. Healing is especially difficult in the avascular (white-white) portions of the meniscus. In addition, chronic tears may be less likely to heal than acute tears, and adult tissue, because of reduced vascularity, may also be less likely to heal. The goal of the study described below was to investigate the feasibility of repairing adult meniscal tissue with chronic tears by using collagenase Materials and Methods Adult bovine knees were obtained fresh and the menisci removed under sterile conditions. The menisci were stored overnight at 4° C. in a solution of DMEM and gentamicin prior to creation of tears in the tissue. An 8-mm biopsy punch was used to punch eight samples from each meniscus. The samples were then trimmed to a 2-mm thickness, and a 3-mm biopsy punch was used to core a section from the center of each 8-mm disk. The center sections and disk portions were kept separate, and all were placed in 12-well culture plates with DMEM growth media supplemented with 10% fetal bovine serum (FBS) and gentamicin. The plates were incubated at 37° C., 5% $CO_2$ for 1 week, with media changed twice per week.

At the end of the 1-week chronic tear period, collagenase solutions were prepared by reconstituting lyophilized collagenase (Worthington Biochemical, Type 2, CLSS-2, 273 U/mg) in D-PBS with calcium chloride. The test articles were submerged in the collagenase solution (1 mg/ml) for 10 minutes and then rinsed thoroughly in PBS. Control test articles were rinsed in PBS only. All test articles were reassembled and incubated at 37° C., 5% $CO_2$ for 3 and 6 weeks in DMEM with 10% FBS and gentamicin. Media changes were done twice weekly.

At the end of 3 and 6 weeks, test articles were fixed in formalin and processed for paraffin embedding. Paraffin sections were stained with H&E and examined using light microscopy. Grades from 0 (no healing) to 3 (complete healing) were used to score the healing seen in the sections.

Results

Histology of test articles revealed that little repair had taken place during the first 3 weeks of incubation. The data are contained in Table 2.

TABLE 2

| Treatment Group | 3-Week Histology Score (mean ± s.d.) | 6-Week Histology Score (mean ± s.d.) |
|---|---|---|
| Untreated Control | 0.7 ± 0.5 | 0.6 ± 0.5 |
| Collagenase | 1.0 ± 0.7 | 1.2 ± 0.7 |

There was no significant difference between the mean histology scores for the collagenase treated and control test articles. None of the test articles at 3 weeks was graded a 3 (complete repair), and only one collagenase treated test article was graded a 2. None of the control test articles received scores greater than 1.

At six weeks, there is a trend toward improvement in histology scores in the collagenase-treated group (mean of 1.25 versus 3-week mean of 1), but the control test article scores did not increase (mean of 0.57 versus 3-week mean of 0.67). The differences between the collagenase-treated test articles and the untreated controls at six weeks was not statistically significant (p=0.059), but showed a definite trend toward improved repair with collagenase.

Discussion and Conclusions

The results showed a trend in improvement in tissue healing when collagenase is used as a treatment, even in adult tissue using a chronic tear model. There was a strong trend toward improved healing at 6 weeks when collagenase is used to treat the meniscal tissue. The collagenase treatment method used for this study was the same as previously used for the acute tear model in bovine calf tissue.

EXAMPLE 3

Surgical Procedure on Human Patient Using Collagenase to Promote Tissue Fusion

A patient is diagnosed with a torn meniscus. The patient is prepped for arthroscopic surgery in a conventional manner, and anesthetized using a conventional anesthetic and conventional anesthesia procedures. Conventional portals are inserted into the patient's knee for access to the surgical site and for insertion of an arthroscope. A saline flow is infused into the knee using a conventional gravity feed or, alternatively, a mechanical pump that controls flow into and out of the knee. The surgeon is able to see a tear in the patient's meniscus. The meniscus is repaired in the following manner. The opposing edges of the meniscus tear are optionally prepared to enhance healing using a small rasp or motorized shaver. The collagenase composition is applied to the tear surfaces, and the meniscal tear is closed using one or more of a variety of tissue approximation conventional devices including; suture, absorbable tacks, or a meniscal repair device. Alternatively, the collagenase composition includes an adhesive. The instruments, scope and cannulas are removed from the patient's knee, and the saline flow stopped. The knee is drained and the incisions for the portals are closed in a conventional manner by suturing. Follow-up examination by a physician shows healing of the tear, indicative of tissue fusion.

Although this invention has been shown and described with respect to detailed embodiments thereof, it will be understood by those skilled in the art that various changes in form and detail thereof may be made without departing from the spirit and scope of the claimed invention.

We claim:

1. A method of healing a defect or injury in meniscal tissue comprising a first surface of the tissue and an opposing second surface of the tissue, the method comprising the steps of:
Applying a collagenase composition to at least one of the first surface or second surface of the defect or injury, and applying a collagenase scavenger solution to a region surrounding the at least one of the first surface or second surface of the defect or injury, thereby promoting fusion of the first surface to the second surface and healing of the defect or injury.

2. The method of claim 1 wherein the collagenase composition is applied in vivo.

3. The method of claim 1, wherein the collagenase composition is selected from the group consisting of matrix metalloproteinase (MMP)-1, MMP-8 and MMP-13.

4. The method of claim 1, wherein the collagenase comprises at least one collagenase produced by bacterium *clostridium hystolyticum*.

5. The method of claim 1, wherein the collagenase composition additionally comprises at least one member of the group consisting of trypsin, caseinase, clostripain, hyaluronidase and combinations thereof.

6. The method of claim 1 wherein the composition additionally comprises an adhesive.

7. The method of claim 1, wherein the defect or injury comprises a tear and wherein an adhesive is applied to the meniscus at the tear to seal and prevent escape of collagenase into the region surrounding the tear.

8. The method of claim 1, wherein the defect or injury comprises a tear and wherein the first meniscal surface and second meniscal surface are apposed by a mechanical repair method following application of collagenase.

9. The method of claim 8 wherein the mechanical repair method comprises a suturing technique.

10. The method of claim 8 wherein the mechanical repair method comprises a barbed or threaded device inserted across the tear which holds the tear faces together.

11. The method of claim 8 wherein the mechanical repair method comprises a hybrid suture/device meniscal repair system.

12. The method of claim 1, wherein the collagenase scavenger solution comprises a collagen solution.

13. The method of claim 1, wherein the collagenase composition comprises a carrier selected from the group consisting of biodegradable surgical mesh, woven fabric, felt, and nonwoven fabric.

14. The method of claim 1 wherein the collagenase composition additionally comprises a nonresorbable carrier comprising a polymer selected from the group consisting of polypropylene, polyethylene, polytetrafluoroethylene (PTFE), polyester and combinations thereof.

15. The method of claim 1, wherein the collagenase is applied to a biocompatible substrate, which is applied to the defect or injury.

16. The method of claim 1 and further comprising applying collagenase composition to both the first surface and the second surface.

* * * * *